United States Patent [19]

Houghton et al.

[11] 4,417,588
[45] Nov. 29, 1983

[54] APPARATUS AND METHOD FOR INITIATING CARDIAC OUTPUT COMPUTATIONS

[75] Inventors: Richard B. Houghton, Irvine, Calif.; David J. Lentz, Salt Lake City, Utah

[73] Assignee: Critikon, Inc., Tampa, Fla.

[21] Appl. No.: 360,942

[22] Filed: Mar. 22, 1982

[51] Int. Cl.³ .............................................. A61B 5/02
[52] U.S. Cl. .................................................. 128/713
[58] Field of Search ........................ 128/713, 691–694; 73/209

[56] References Cited

U.S. PATENT DOCUMENTS

| | | | |
|---|---|---|---|
| 3,987,788 | 10/1976 | Emil | 128/713 |
| 4,015,593 | 4/1977 | Elings et al. | 128/713 |
| 4,273,136 | 6/1981 | Kubo et al. | 128/681 X |
| 4,361,049 | 11/1982 | Volgyesi | 128/713 X |

OTHER PUBLICATIONS

Devi, V. L. et al., "A Processing System for Automatic On-Line LVET Determination," Conf: Proc. of IFIP-IMIA Conf., Rome, Italy, Feb. 6-8, 1980, pp. 167-173.

Primary Examiner—Kyle L. Howell
Assistant Examiner—Francis J. Jaworski
Attorney, Agent, or Firm—Michael A. Kaufman

[57] ABSTRACT

A cardiac output computer which measures cardiac output by the indicator method involving the estimation of the area under either a thermodilution of a luminous transmission curve with automatic bolus detection. Evaluation of the area under the curve is made relative to a true baseline and is independent of, in the case of thermodilution, blood temperature as of the time the bolus is injected into the patient. A series of blood temperature samples are read and stored with the magnitude of each successive signal compared to the one received immediately before. As soon as a plurality of successive comparisons, preferably five, of six successively acquired blood temperatures indicate monotonically decreasing blood temperature values, a test for monotonicity is confirmed, with the highest temperature of the six being designated as the baseline. Once the test is confirmed the computer proceeds to evaluate the area under the curve.

9 Claims, 6 Drawing Figures

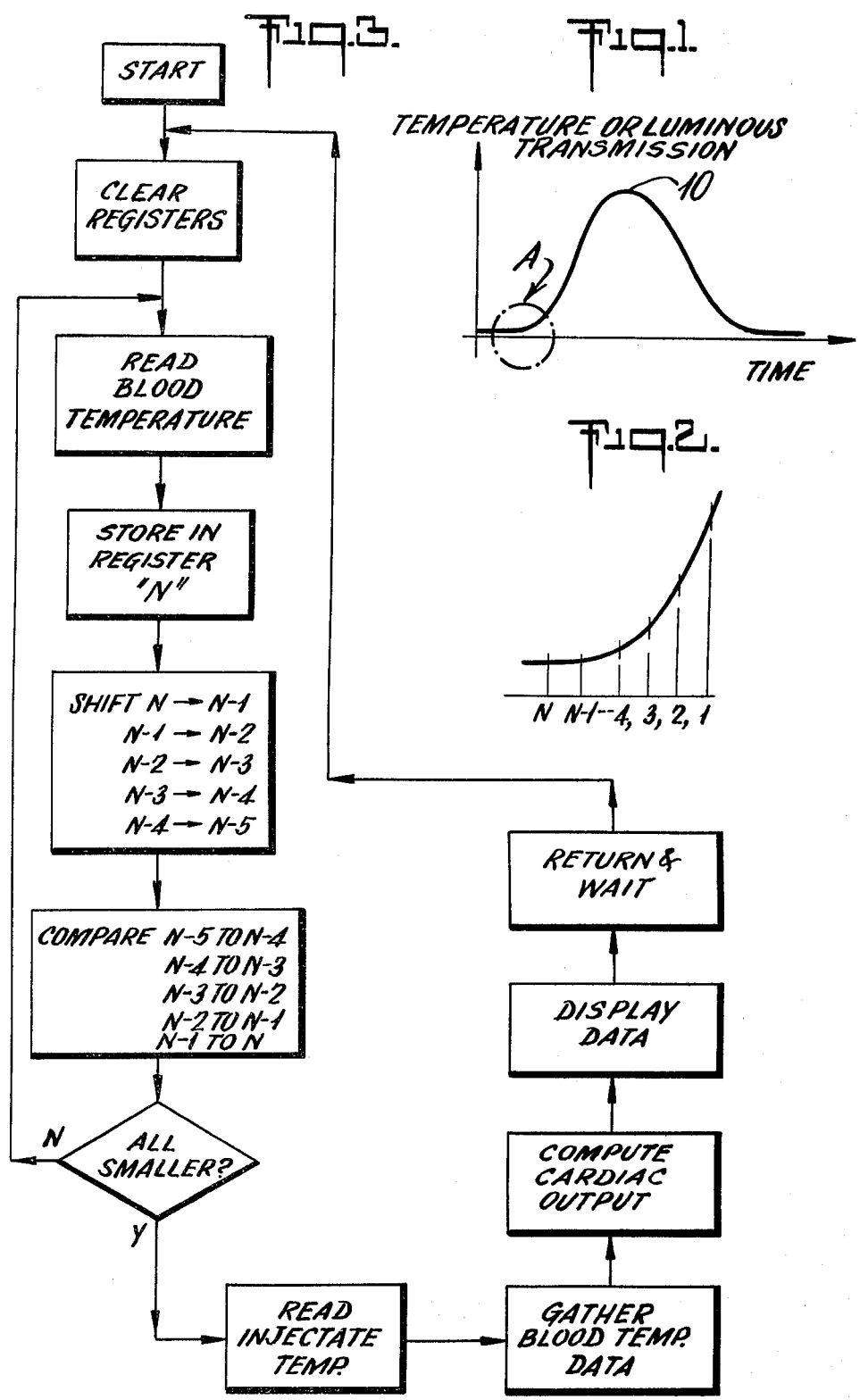

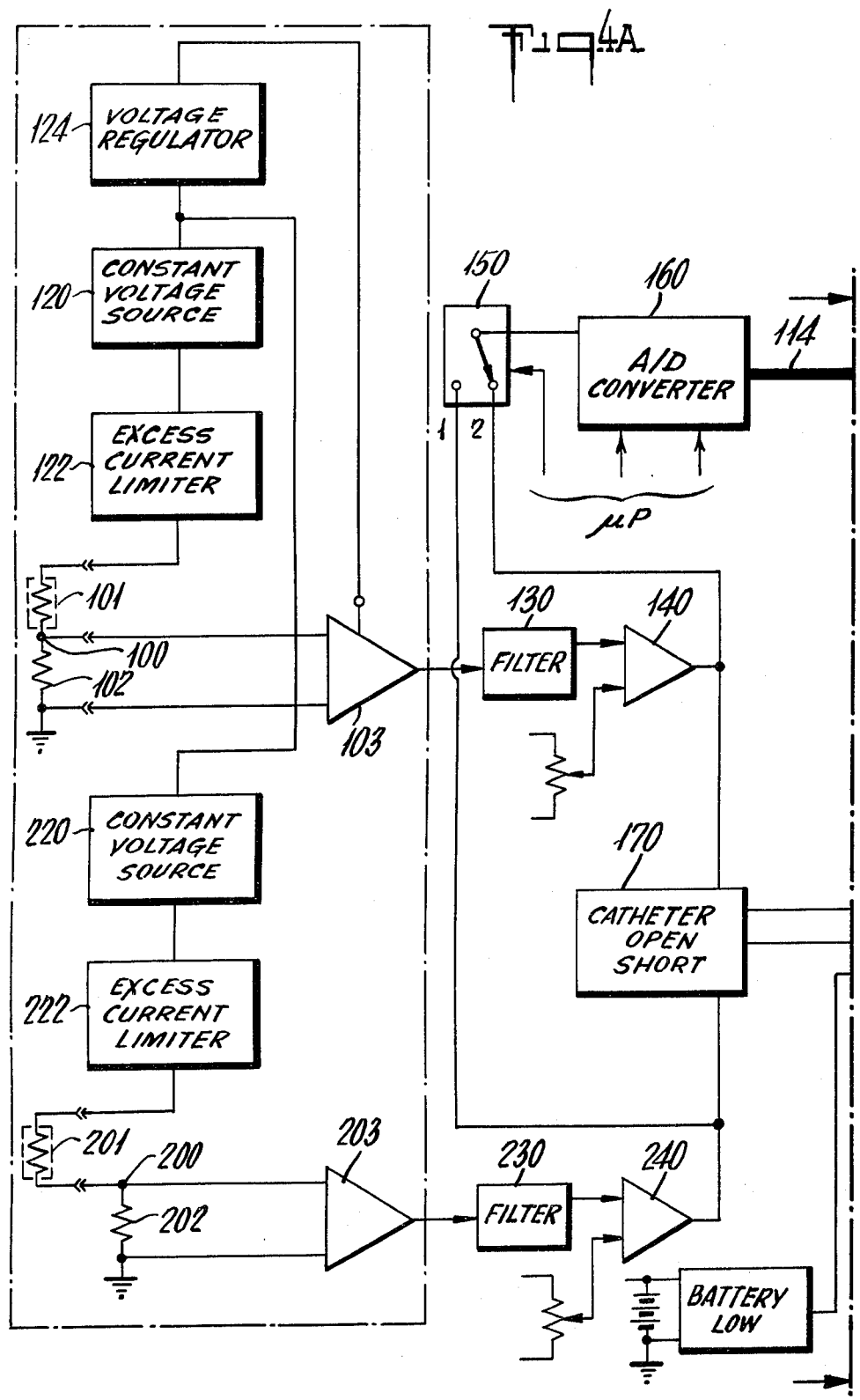

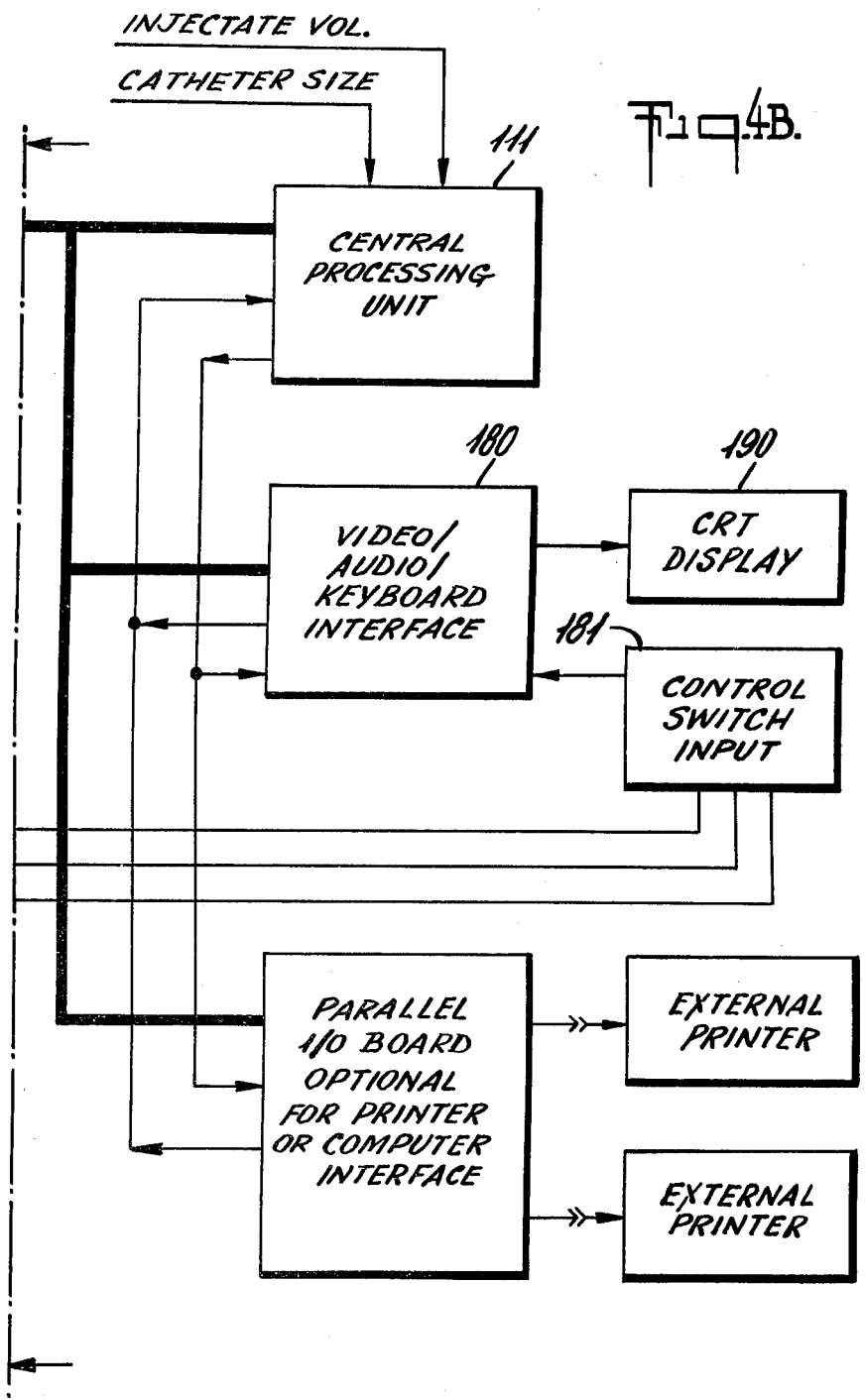

APPARATUS AND METHOD FOR INITIATING CARDIAC OUTPUT COMPUTATIONS

TECHNICAL FIELD OF THE INVENTION

This invention relates to the measurement of cardiac output and in particular to a technique for improving accuracy by timimg the initiation of cardiac output computations.

BACKGROUND ART

By definition, the rate of blood flow at any point in the cardiovascular system is expressed as the volume of blood that passes that point during a unit of time. Since an adequate blood supply is essential for all organs in the body, a measure of blood flow in a vessel that supplies a particular organ is of invaluable diagnostic importance. The blood flow rate is greatest in the pulmonary artery and the aorta, where the blood vessel leaves the heart. The flow at these points is called cardiac output.

There are numerous techniques available for the measurement of cardiac output. A well known one makes use of the principals of indicator (dye or thermal) dilution. In thermodilution systems, a small quantity of an indicator having a temperature typically lower than that of blood is introduced into the circulatory system and a thermistor is used to sense the temperature of the blood at a location downstream of the introduction site. As the cool indicator travels through the blood stream toward the thermistor location, the temperature of the blood temporarily decreases as its temperature is diluted by the indicator. Temporal variations in blood temperature resulting from the introduction of the indicator into the blood stream are sensed by the thermistor and are used to compute the blood flow rate or cardiac output. A plot of the changes in blood temperature as a function of time is referred to as a thermodilution curve, and the cardiac output is determined by measuring the area under this curve. A representative system for computing cardiac flow rates from thermodilution measurements is disclosed in U.S. Pat. No. 3,987,788 to Emil.

Alternatively, the indicator injected into the circulatory system may be a volume of non-toxic dye. The injected dye has a detectable light absorption characteristic different than that of blood and hence yields a densitometric output curve with the same generalized profile as a thermodilution curve. The variations in the amplitude of the detected data from either the thermodilution or the dye injection method may then be processed by the Stewart-Hamilton equation to yield cardiac output. The solution to the Stewart-Hamilton equation requires the integration of either the blood temperature change with time or the dye concentration change with time.

Much has been written about the inaccuracies of various integration techniques for estimating the area under the output curve. Inaccuracies stem, for example, from recirculation of the blood past the point of measurement, since the indicator is not dissipated immediately by the body, but may pass repeatedly through the heart, or from baseline drifts that lead to large errors if a long integration time is used. See, for example, U.S. Pat. No. 4,015,593 to Elings et al. However, error introduced into the calculation by spurious changes in blood temperature independent of the introduction of the injectate have been ignored. Thus, in conventional cardiac output computations, a start button is depressed to indicate to a computer that the injectate has been or will be made. The baseline for the integration calculations is established based on the temperature of the blood as of the time the button is depressed and held pending the integration of the curve. Since several seconds may elapse before the indicator or the bolus of injectate reaches the sensing device, the baseline may shift. Thus, establishing the blood temperature baseline as of this earlier time is inaccurate and may introduce considerable error into the computations since the integration is done with respect to the established baseline. The error introduced in such a system is proportional to the integral of the difference between the true baseline and the measured baseline at the start switch time over the integration time period.

DISCLOSURE OF THE INVENTION

We have invented a system for measuring cardiac output with improved accuracy by generating a more accurate baseline which is independent of the time of introduction of the indicator. Our invention automatically detects the bolus of injectate at the situs of interest thereby yielding a true baseline blood temperature and hence a more accurate cardiac output measurement.

A method and apparatus for initiating a cardiac output flow rate measurement which may be utilized in connection with either thermodilution or dye injection techniques is disclosed. In accordance with our invention, a known volume of liquid at a reduced temperature relative to that of blood or a volume of non-toxic dye is injected into the circulatory system. In case of the former, the preferred embodiment, the temperature of the blood is temporarily reduced by the lower temperature of the injected liquid. This produces a reduced temperature profile as a function of time. The temperature of the blood at a specified location is continually sampled and a signal that is a function of the blood temperature at each of the sampling times is stored in one of a series of registers or in a stage of a multi-stage register. At each sampling time, the most recently acquired temperature is sensed and transmitted to a first register, with each previously sampled temperature shifted to an adjacent register and with the data in the last register being deleted. Contemporaneously, the magnitude of the signal in the first register is compared to that in the second to determine the directional change in the temperature of the blood. As soon as a predetermined plurality, preferably five, of successive comparisons all yield monotonically decreasing temperature values, the baseline temperature is established as the highest temperature in the comparison chain and computation of the area under the thermodilution curve is initiated.

BRIEF DESCRIPTION OF THE DRAWINGS

FIG. 1 is an inverted diagrammatical representation of a thermodilution curve or luminous transmission curve representing either blood temperature change with respect to time or luminous transmission variations in the blood with respect to time.

FIG. 2 is a detail of the area indicated by the letter A in FIG. 1 showing the upslope in the thermodilution or luminous transmission curve, with the value of N corresponding to and representing the baseline.

FIG. 3 is a flow chart of a method for obtaining cardiac output according to the present invention.

FIGS. 4A and 4B taken together is a schematic representation in block diagram form depicting an illustrative embodiment of a cardiac output computer in accordance with the invention.

DESCRIPTION

Figure 4C:
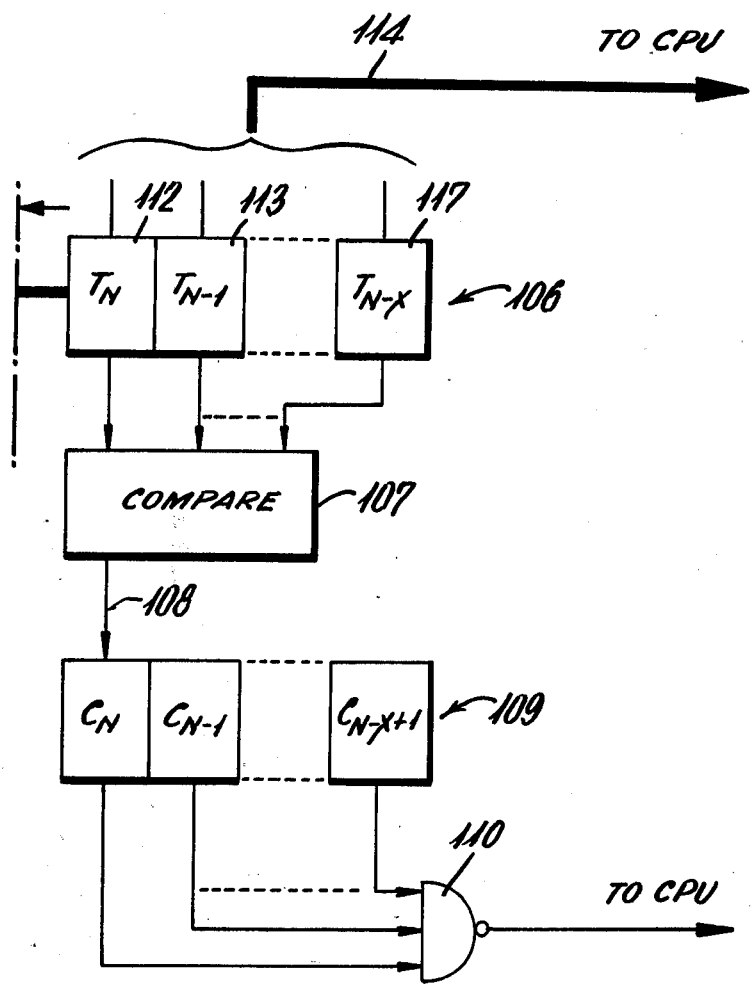
FIG. 4C is a schematic block diagram of a portion of FIGS. 4A and 4B showing the baseline acquisition and initiation of the cardiac output computation in hard wired logic.

The attached drawings show, in schematic apparatus form, a preferred embodiment of a system and technique for automatic bolus detection free of error due to spurious baseline shift. It is to be noted that, depending upon the predilection of the designer, the availability of specified parts, and the general technical capacity of the designer, the principles of the present invention may be employed to advantage both in a microprocessor based computational system, or in terms of more traditional hard wired logic. The schematic representations set forth in the attached drawing are believed sufficient to be readily understood and applied by those of ordinary skill either in the hard wired logic or the software and microprocessor arts to make and use the invention.

Referring first to FIG. 4, a thermosensor such as thermistor 101 is biased in conventional fashion with a constant voltage source 120 protected by an excess current limiter 122 such as a series limiting resistor Rs and a voltage regulator 124. The thermistor 101 is in a resistance divider configuration with a resistor 102, and the signal at the midpoint 100 is coupled to a signal conditioning and, as desired, patient-isolating amplifier 103. The signal is further conditioned by a 10 Hz filter 130 and the reference point shifted by a zero-offset amplifier 140 before being coupled to an analog to digital converter 160 through a solid state switch 150. The catheter containing thermistor 101 is adapted to be introduced into a subject's circulatory system and located at a desired point therein, typically, for cardiac output measurement, in the pulmonary artery or the aorta, where the blood vessels leave the heart.

A second thermistor 201 serves as an injectate probe for providing a signal that is a function of the injectate or indicator temperature. Thermistor 201 is also provided with a constant voltage source 220 and an excess current limiter 222, in parallel with constant voltage source 120 and excess current limiter 122. Both voltage sources are regulated by the same voltage regulator 124. Similarly, thermistor 201 is in a resistance divider configuration with resistor 202, and the signal at the midpoint 200 is coupled to a signal conditioning and patient-isolating amplifier 203.

The output signal of amplifier 203 is in like fashion further conditioned by a 10 Hz filter 230 and its reference point shifted by a zero-offset amplifier 240 before being coupled to the A to D converter 160 through solid state switch 150.

The analog signal output by the two zero-offset amplifiers 140 and 240 are alternately digitized by the single A to D, converter with the switch 150 controlling the sequence. The use of a single A to D converter and switch combination is an economy measure which could be replaced by a separate A to D converter for each thermistor signal. Both the solid state switch and the A to D converter are under microprocessor control. Thus, the source of the digital signal processed by the A to D converter is known.

It will be appreciated that the sampling rate employed at switch 150 will be based on the anticipated circulatory/thermal characteristics of the circulatory system (e.g., human, animal, adult, child, etc.) it being understood that the sampling rate must be sufficiently rapid such that in the cardiac output evaluating and integrating process, there results a smooth, rather than a stepwise granular cardiac output curve.

Samples are converted to digital form at the A to D converter 160, for example, by employing an 8 bit binary format, thereby yielding 4096 encoding levels. The 12 bit encoded samples are successively coupled to a shift register 106 of x+1 stages wherein, each stage 112, 113, etc. stores a digital representation of a different successive blood temperature sample, for example, in bit parallel fashion. Conventionally, as each blood temperature sample is coupled to a first stage 112 of the register 106, each succeeding blood temperature sample is advanced to the next, with the blood temperature sample in the last stage 117 being discarded. Hence, at any given time, a succession of x+1 successive encoded blood temperature samples are maintained in storage in the register 106. In a preferred embodiment, register 106 employs six stages, each stage carrying an 8 bit binary word representative of one of a succession of six blood temperature samples.

In accordance with the principles of the present invention, an injectate also referred to as bolus is deemed not to occur unless x (in the preferred embodiment, five) successive blood temperature samples in register 106 demonstrate monotonically decreasing temperature amplitudes. It is to be noted that while conventional cardiac output curves are shown with first a positively tending, then a negatively tending curve, e.g. as illustrated in FIG. 1, in fact the measured blood temperature first drops as a function of the bolus, and then returns positively in approximate exponential fashion to the normal temperature. Accordingly, the principles of the present invention seek monotonic decreases of temperature samples in the register 106, although the eventual curve will show corresponding monotonic increases in cardiac output curve.

In accordance with the hard wired logic embodiment shown in FIG. 4C, monotonicity is detected by means of a comparison function performed by comparator 107, which compares the amplitudes of the two temperatures, designated $T_N$ and $T_{N-1}$ in the first two stages 112, 113 of register 106, producing a single bit logical indicator at line 108, depending on which of the samples $T_N$ and $T_{N-1}$ is the larger. For example, it is appropriate to adopt the convention that a bit $C_N$ is a logical 0 if sample $T_{N-1}$ is smaller than sample $T_N$, and is a logical 1 if the converse is true. Accordingly, register 109 stores a plurality of comparison bits $C_N$ through $C_{N-x+1}$ (in the preferred embodiment, five), which represent the amplitude differentials between corresponding successive samples in the register 106.

A NAND gate 110 senses all of the comparison bits $C_N$ through $C_{N-x+1}$ in register 109, issuing a logical 1 at its output whenever all bits in register 109 are logical 0. Thus, a logical 1 bit at the output of NAND gate 110 represents monotonic decreases in all the successive samples in register 106. Therefore, the logical 1 output from gate 110 causes a central processing unit (CPU) to commence the integration operations for producing a cardiac output curve. To this end, upon receipt of a logical 1 from gate 110, the CPU reads, via line 114, each of the blood temperature samples then stored in register 106, with the temperature sample stored in stage $T_{N-x}$ representing the initial blood temperature, i.e., the baseline. The CPU also reads the injectate volume and temperature, and the catheter size. Based on these quantities, and thereafter upon succeeding encoded temperature samples (read either successively from the first stage 112 of register 106, or, as desired, directly from A to D converter 160), the CPU proceeds to evaluate the cardiac output function in accordance with the Stewart-Hamilton equation, which in the case of thermodilution is:

$$C.O. = \frac{0.0648\,(TB - TI) \times C_T \times V_I}{\int_0^\infty dTB\,(t)\,dt}$$

Where:

C.O. = Cardiac output in (l/min.)

.0648 =

$$\frac{\text{(Specific heat} \times \text{specific gravity of the injectate)} \times 60\ \text{sec/min}}{\text{(Specific heat} \times \text{specific gravity of blood)} \times 1000\ \text{ml/l}}$$

Injectate: 5% dextrose solution (D5W)
TB = Initial blood temperature in °C.
TI = Initial injectate temperature in °C.
C = Correction factor for injectate temperature rise through the catheter
$V_I$ = Volume of injectate in ml $$\int_0^\infty dTB\,(t)\,dt = \text{Integral of the blood temperature change with time}$$

In the case of dye dilution, cardiac output is represented by the formula:

$$C.O. = \frac{I}{\int Cg(t)dt} \times 60$$

where:
C.O. = cardiac output (l/min)
I = amount of dye injected into venous circulation (mg)
Cg(t) = instantaneous dye concentration in arterial blood (mg/l)
t = time (sec)

The discrete components shown in FIG. 4C and described hereinabove may be dispensed with if it is desired to use a programmable system for detecting monotonicity. If so, the microprocessor based computational system as shown in FIG. 4B is utilized in accordance with the sequence of steps delineated in the flow chart of FIG. 3.

The microprocessor system comprises, for example, a CDP 185603 computer with an 8K ROM and a 2K RAM in communicating relation with a CDP 185661 video/audio/keyboard interface 180 and a CDP 185646 parallel input/output board with optical printer or computer interface 182. Signals from zero offset amplifiers 140 and 240 are sequentially coupled to the A to D converter 160 by the solid state switch 150 which alternates contact with the two input lines 1 and 2. The A to D converter, in turn, converts each analog signal to digital form without distinguishing as to the source of the signal. The digital output of the converter is placed into memory via the Data Bus line 114. To distinguish the data representing blood temperature from data representing indicator or bolus temperature, the memory locations are coded in response to the position of the switch. Thus, one area of memory is utilized for digital data representative of blood temperature and another area of memory (or a separate memory) is utilized for digital data representative of indicator temperature.

With the computer on, catheter temperature and injectate temperatures are alternately sampled at a rate controlled by the changes in the state of the solid state switch 150 whose operation is under microprocessor control. When the solid state switch is sampling the output of zero-offset amplifier 140, the output of zero-offset amplifier 240 is fed into the computer by a catheter open short function 170. The catheter open short 170 has an open and a short line which are coupled to the video/audio/keyboard interface 180 of the computer by means of control switch input 181. Similarly, when the injectate temperature is being sampled, that is, when the output of zero-offset amplifier 240 is being digitized, the output of the other offset amplifier 140 is fed into the video/audio/keyboard interface 180 by catheter open short 170 and control switch input 181.

When the computer power is turned on, all of the storage registers in the computer's memory are cleared and the catheter diameter is read. Blood temperature and injectate temperature samples are sequentially read with the first blood temperature sample stroed in a first or a baseline register. As the next temperature sample is read, data from the first register is shifted to the second register with the new temperature value read into the baseline register. Intermittently, the injectate temperature is read and stroed in an injectate temperature register. There are N blood temperature registers but only one injectate register. The value in each blood temperature register is compared with the next higher address register. If all the values are greater, a test for increasing monotonicity is confirmed. This indicates that the dilution curve is rising (in the inverted convention) as shown in FIGS. 1 and 2. If the test for increasing monotonicity is not confirmed, the computer returns to the baseline acquisition subroutine and continues until the upslope is detected. Any number of samples may be selected to insure monotonicity, however, the preferred number of samples is 6 yielding 5 comparisons. The injectate temperature is continually upgraded in the injectate register until the monotonicity test is confirmed.

Once the test for monotonicity is confirmed, the computations for estimating the cardiac output is commenced with the temperature in register N serving as the baseline temperature and the data in the injectate temperature register serving as the initial injectate temperature. At this point, the injectate temperatures are no longer sampled, although the catheter continues to be sampled on a predetermined time basis controlled by the computer.

Estimation of the area under the thermodilution curve may then be processed in accordance with well-known integration techniques wherein the integration may extend from the time the upswing is detected until a specified period of time has elapsed or until a preselected percentage of the peak value 10 of the curve is detected on the downslope side with the remaining area being estimated. The thermodilution curve may be displayed on a CRT display 190.

The above described techniques using either the hard wired logic illustrated in FIG. 4C or the programmed method may similarly be employed in connection with dye dilution in precisely the same sequence.

We claim:

1. In an apparatus for measuring cardiac output flow rate by introducing a predetermined amount of an indicator at a known temperature into the blood stream of a subject and monitoring the temperature of the blood at a location downstream from the point of introduction, including blood temperature sampling means for generating time dependent signals representative of the varying blood temperature at said location as said indicator travels through the bloodstream relative to said location, said signals defining a thermodilution curve, computing means for estimating the area bounded by said thermodilution curve and a baseline temperature subsequent to a first point in time, the improvement comprising:
   (a) comparing means for comparing successive signals;
   (b) means responsive to said comparing means for designating as said baseline temperature the temperature that corresponds to the first signal that is followed by a predetermined plurality of signals each representing a successively decreasing blood temperature, said first signal representing blood temperature at said first time; and
   (c) means for initiating said computing means in response to designating said baseline temperature.

2. In the apparatus according to claim 1 wherein said comparing means includes:
   (a) a first multi-stage shift register for storing a predetermined plurality of digitized blood temperature signals and shifting the contents of each stage in a predetermined sequence as each new signal is received;
   (b) a comparator for comparing the magnitude of the signals in two of the stages of said first shift register, said comparator having an output for issuing a first signal when the comparison indicates a rise in temperature and a second signal when the comparison indicates a decline in temperature; and
   (c) a second multi-stage register coupled to the output of said comparator for sequentially storing in each of its stages an output signal received from said comparator.

3. In an apparatus according to claim 2 wherein said means for initiating said computing means includes a multiple input NAND gate, wherein each of the inputs to said NAND gate connect to one of the stages of said second multi-stage register.

4. In an apparatus according to either of claims 2 or 3 wherein said first register comprises at least six stages and said second register comprises one stage less than said first register.

5. In an apparatus for measuring cardiac output flow rate by introducing into the bloodstream of a subject a predetermined quantity of an indicator dye having a known detectable absorption characteristic different from that of said blood and monitoring the changes in light absorption of the blood at a location downstream from the point of introduction, including blood light absorption sampling means for generating time dependent signals representative of the varying blood light absorption at said location as said indicator travels through the bloodstream relative to said location, said signals defining a luminous transmission curve, computing means for estimating the area bounded by said luminous transmission curve and a baseline of light absorption subsequent to a first point in time, the improvement comprising:
   (a) comparing means for comparing successive signals;
   (b) means responsive to said comparing means for designating as said baseline, the light absorption corresponding to the first signal that is followed by a predetermined plurality of signals each representing a successively decreasing level of light detection, said first signal representing light absorption at said first time; and
   (c) means for initiating said computing means in response to designating said baseline of light absorption.

6. A method of measuring cardiac output comprising:
   (a) introducing a known volume of an indicator at a known temperature into the blood stream of a subject;
   (b) sensing blood temperature at a specified location within said subject;
   (c) sampling said blood temperature at predetermined intervals to form a blood temperature profile;
   (d) comparing successive blood temperature values;
   (e) designating as a baseline temperature the first temperature sampled subsequent to introducing the indicator which is followed by a predetermined plurality of successively decreasing blood temperatures, wherein said first temperature corresponds to a first time; and
   (f) estimating cardiac output by steps including integrating the area between said baseline temperature and said blood temperature profile over a specified period commencing with said first time.

7. A method of measuring cardiac output according to claim 6 wherein at least five successive decreases in blood blood temperature are sampled before a baseline is designated.

8. A method of measuring cardiac output comprising:
   (a) introducing into the bloodstream of a subject a known volume of an indicator dye having a detectable light absorption characteristic different from that of the subject's blood;
   (b) detecting blood light absorption at a specified location within said subject;
   (c) sampling said blood light detection at predetermined intervals to form a luminous transmission curve;
   (d) designating as a baseline the first blood light absorption value sampled subsequent to introducing the dye which is followed by a predetermined plurality of successively decreasing light absorption detection signals, wherein said first light absorption signal corresponds to a first time; and
   (e) estimating cardiac output by steps including estimating the area between said baseline and said luminous transmission curve over a specified period commencing with said first time.

9. A method of measuring cardiac output according to claim 8 wherein at least five successive decreases in blood light absorption are sampled before a baseline is designated.

* * * * *